(12) United States Patent
Ji et al.

(10) Patent No.: US 6,451,577 B1
(45) Date of Patent: Sep. 17, 2002

(54) HUMAN URIDINE DISPHOSPHATE GALACTOSE-4-EPIMERASE

(75) Inventors: Hongjun Ji, Germantown, MD (US); Craig A. Rosen, Laytonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/624,183

(22) Filed: Jul. 24, 2000

Related U.S. Application Data

(62) Division of application No. 09/113,536, filed on Jul. 10, 1998, now Pat. No. 6,153,739, which is a continuation of application No. 08/462,966, filed on Jun. 5, 1995, now abandoned, which is a continuation of application No. PCT/US95/05785, filed on May 11, 1995.

(51) Int. Cl.[7] .............................. C12N 9/90; C12N 1/20; C12N 15/00; C12Q 1/68; C07H 21/04
(52) U.S. Cl. ........................ 435/233; 435/6; 435/252.3; 435/440; 536/23.2
(58) Field of Search ........................ 435/233, 6, 252.3, 435/440; 536/23.2

(56) References Cited

U.S. PATENT DOCUMENTS

| | | | | |
|---|---|---|---|---|
| 5,135,854 A | * | 8/1992 | MacKay | ..................... 435/69.1 |
| 5,542,935 A | * | 8/1996 | Unger et al. | .......... 128/999.999 |
| 5,726,044 A | * | 3/1998 | Lo et al. | ..................... 435/69.7 |

FOREIGN PATENT DOCUMENTS

WO 94/18331 8/1994

OTHER PUBLICATIONS

Zeschnigk et al., "cDNA from rat cells with reconstitutive galactose–epimerase activity in *E. coli*", Nucl. Acids. Res., 18(17):5289 (1990).

Peng et al., "Cloning and Expression of the *Klebsiella pneumoniae* Galactose Operon", J. Biochem., 112:604–608 (1992).

Metzger et al., "Genetics of Galactose Metabolism of *Erwinia amylovora* and Its Influence on Polysaccaride Synthesis . . . ", J. Bacteriol., 176(2):450–459 (1994).

Lin et al., "Assignment of the Gene for Uridine Diphosphate Galactose–4–Epimerase to Human Chromosome 1 by Human–Mouse . . . ", Somatic Cell Genetics, 5(3):138–142 (1979).

Benn et al., "Assignment of a Gene for uridine diphosphate galatose–4–epimerase to human chromosome 1 by somatic . . . ", Cytogenet. Cell Genet., 24(3):138–142 (1979).

Daude et al., "Molecular Cloning, Characterization, and Mapping of a Full–Length cDNA Encoding Human . . . ", Biochem. and Mol. Med., 56: 1–7 (1995).

Webster et al., "Nucleotide Sequence of the galactose gene cluster of . . . ", Nucl. Acids Res., 16(16):8192–8194 (1988).

Jaye et al., "Isolation of a human anti–haemophilic factor IX cDNA clone using . . . ", Nucl. Acids Res., 11(8):2325–2335 (1983).

* cited by examiner

Primary Examiner—Ponnathapu Achutamurthy
(74) Attorney, Agent, or Firm—Human Genome Sciences, Inc.

(57) ABSTRACT

A human UDP galactose-4-epimerase polypeptide and DNA (RNA) encoding such polypeptide and a procedure for producing such polypeptide by recombinant techniques is disclosed. Also disclosed are methods for utilizing such polypeptide for the treatment of galactosemia. Also disclosed are diagnostic assays for the detection of mutations in the nucleic acid sequencing encoding human UDP galactose-4-epimerase protein and for detecting an altered level of human UDP galactose-4-epimerase protein in a sample derived from a host.

18 Claims, 3 Drawing Sheets

```
GGCACGAGCCGAGCAGGACTCTCCAGTCCTCAGTCACCTTGGACAAAGAAGTGTGGATCC
TCAGATTCCATCTTTTCCAACTCCAAGGTGCCATGGCAGAGAAGGTGCTGGTAACAGGTG
                                M A E K V L V T G G
GGGCTGGCTACATTGGCAGCCACACGGTGCTGGAGCTGCTGGAGGCTGGCTACTTGCCTG
 A G Y I G S H T V L E L L E A G Y L P V
TGGTCATCGATAACTTCCATAATGCCTTCCGTGGAGGGGGCTCCCTGCCTGAGAGCCTGC
 V I D N F H N A F R G G G S L P E S L R
GGCGGGTCCAGGAGCTGACAGGCCGCTCTGTGGAGTTTGAGGAGATGGACATTTTGGACC
 R V Q E L T G R S V E F E E M D I L D Q
AGGGAGCCCTACAGCGTCTCTTCAAAAAGTACAGCTTTATGGCGGTCATCCACTTTGCGG
 G A L Q R L F K K Y S F M A V I H F A G
GGCTCAAGGCCGTGGGCGAGTCGGTGCAGAAGCCTCTGGATTATTACAGAGTTAACCTGA
 L K A V G E S V Q K P L D Y Y R V N L T
CCGGGACCATCCAGCTTCTGGAGATCATGAAGGCCCACGGGGTGAAGAACCTGGTGTTCA
 G T I Q L L E I M K A H G V K N L V F S
GCAGCTCAGCCACTGTGTACGGGAACCCCCAGTACCTGCCCCTTGATGAGGCCCACCCCA
 S S A T V Y G N P Q Y L P L D E A H P T
CGGGTGGTTGTACCAACCCTTACGGCAAGTCCAAGTTCTTCATCGAGGAAATGATCCGG
 G G C T N P Y G K S K F F I E E M I R D
```

```
ACCTGTGCCAGGCAGACAAGACTTGGAACGCAGTGCTGCTGCGCTATTTCAACCCCACAG
 L C Q A D K T W N A V L L R Y F N P T G
GTGCCCATGCCTCTGGCTGCATTGGTGAGGATCCCCAGGGCATACCCAACAACCTCATGC
 A H A S G C I G E D P Q G I P N N L M P
CTTATGTCTCCCAGGTGGCGATCGGGCGACGGGAGGCCCTGAATGTCTTTGGCAATGACT
 Y V S Q V A I G R R E A L N V F G N D Y
ATGACACAGAGGATGGCACAGGTGTCCGGGATTACATCCATGTCGTGGATCTGGCCAAGG
 D T E D G T G V R D Y I H V V D L A K G
GCCACATTGCAGCCTTAAGGAAGCTGAAAGAACAGTGTGGCTGCCGGATCTACAACCTGG
 H I A A L R K L K E Q C G C R I Y N L G
GCACGGGCACAGGCTATTCAGTGCTGCAGATGGTCCAGGCTATGGAGAAGGTCTCTGGGA
 T G T G Y S V L Q M V Q A M E K V S G K
AGAAGATCCCGTACAAGGTGGTGGCACGGCGGGAAGGTGATGTGGCAGTCTGTTACGCCA
 K I P Y K V V A R R E G D V A V C Y A N
ACCCCAGTCTGGCCCAAGAGGAGCTGGGGTGGACAGCAGCCTTAGGGCTGGACAGGATGT
 P S L A Q E E L G W T A A L G L D R M C
GTGAGGATCTCTGGCGCTGGCAGAAGCAGAATCCTTCAGGCTTTGGCACGCAAGCCTGAG
 E D L W R W Q K Q N P S G F G T Q A *
GACCCTCCCCTACCAAGGACCAGGAAAAGGAGGAGGTGTCTGCTCTCCAGCCTCTGGGAG
GAACTCAGGGCCCTGGAGCTTGTGGGGACAAGACAAGGTCTCCCCTCTC
```

FIG. 1A

```
GGCACGAGCCGAGCAGGACTCTCCAGTCCTCACCTTGGACAAAGAAGTGTGGATCC
TCAGATTCCATCTTTTCCAACTTCCAAGTGCCATGGCCGAGAAGGTGCTGGTAACAGGTG
                               M  A  E  K  V  L  V  T  G  G

GGGCTGGCTACATTGGCAGCCACACGGTGCTGGAGCTGCTGGAGGCTGGCTACTTGCCTG
 A  G  Y  I  G  S  H  T  V  L  E  L  L  E  A  G  Y  L  P  V

TGGTCATCGATAACTTCCATAATGCCTTCCGTGGAGGGTCCCTGCCTGAGAGCCTGC
 V  I  D  N  F  H  N  A  F  R  G  G  S  L  P  E  S  L  R

GGCGGGTCCAGGAGCTGACAGGCCGCTCTGTGGAGTTTGAGGAGATGGACATTTTGGACC
 R  V  Q  E  L  T  G  R  S  V  E  F  E  E  M  D  I  L  D  Q

AGGGAGCCCTACAGCGTCTCTTCAAAAGTACAGCTTTATGGCGGTCATCCACTTTGCGG
 G  A  L  Q  R  L  F  F  K  K  Y  S  F  M  A  V  I  H  F  A  G

GGCTCAAGGCCGTGGGCGAGTCGGTGCAGAAGCCTCTGGATTATTACAGAGTTAACCTGA
 L  K  A  V  G  E  S  V  Q  K  P  L  D  Y  Y  R  V  N  L  T

CCGGGACCATCCAGCTTCTGGAGATCATGAAGGCCCACGGGTGAAGAACCTGGTGTTCA
 G  T  I  Q  L  L  E  I  M  K  A  H  G  V  K  N  L  V  F  S

GCAGCTCAGCTGTGTACGGGAACCCCAGTACCTGCCCCTTGATGAGGCCCACCCCA
 S  S  A  T  V  Y  G  N  P  Q  Y  L  P  L  D  E  A  H  P  T

CGGGTGGTTGTACCAACCCTTACGGCAAGTCCAAGTTCTTCATCGAGGAAATGATCCGGG
 G  G  C  T  N  P  Y  G  K  S  K  F  F  I  E  E  M  I  R  D
```

FIG. 1B

ACCTGTGCCAGGCAGACAAGACTTGGAACGCAGTGCTGCTATTTCAACCCACAG
 L  C  Q  A  D  K  T  W  N  A  V  L  L  R  Y  F  N  P  T  G
GTGCCCATGCCTCTGGCTGCTGCATTGGTGAGGATCCCAACAACCTCATGC
 A  H  A  S  G  C  I  G  E  D  P  Q  G  I  P  N  N  L  M  P
CTTATGTCTCCCAGTGGCAGGCGATCGGCGACGGAGCCCTGAATGTCTTTGGCAATGACT
 Y  V  S  Q  V  A  I  G  R  R  E  A  L  N  V  F  G  N  D  Y
ATGACACAGAGGATGGCACAGGTGTCCCGGATTACATCCATGTCGTGGATCTGGCCAAGG
 D  T  E  D  G  T  G  V  R  D  Y  I  H  V  V  D  L  A  K  G
GCCACATTGCAGCCTTAAGGAAGCTGAAAGAACAGTGTGGCTGCCGGATCTACAACCTGG
 H  I  A  A  L  R  K  L  K  E  Q  C  G  C  R  I  Y  N  L  G
GCACGGGCACAGGCTATTCAGTGCTGCAGATGGTCCAGGCTATGGAGAAGGTCTCTGGA
 T  G  T  G  Y  S  V  L  Q  M  V  Q  A  M  E  K  V  S  G  K
AGAAGATCCCGTACAAGGTGGTGGCCAGGAGAGAGGGTGGGGCTGGACAGCCTTAGGCTGGACAGGATGT
 K  I  P  Y  K  V  V  A  R  R  E  G  D  V  A  V  C  Y  A  N
ACCCCAGTCTCTGGCCCAAGAGGAGCTGGGGCTGGGTAACAGCAGAATCCTTCAGGCTTGGCACGCAGGATGT
 P  S  L  A  Q  E  E  L  G  W  T  A  A  L  G  L  D  R  M  C
GTGAGGATCTCTGGCCGCTGGCAGAAGCAGAATCCTTCAGGCTTGCACGCAAGCCTGAG
 E  D  L  W  R  W  Q  K  Q  N  P  S  G  F  G  T  Q  A  *
GACCCTCCCTACCAAGGACCAGGAGGACCAGAAAAGGAGGAGTGTCTCTCCAGCCTCTGGGAG
GAACTCAGGGCCCTGGAGCTTGTGTGGGGACAAGACAAGTCTCCCCTCTC

FIG. 2

```
  1 MAEKVLVTGGAGYIGSHTVLELLEAGYLPVVIDNFHNAFRGGGSLPESLR   50
    |.|||||||||||||||||||||||||||||||||||..:|:.:|||||
  1 MEEKVLVTGGAGYIGSHTVLELLEAGYSPVVIDNFHNSIRGEDSMPESLR   50

51 RVQELTGRSVEFEEMDILDQGALQRLFKKYSFMAVIHFAGLKAVGESVQK  100
    ||||||||||||||||||||||:|||:...|.|.||||||||||||||
 51 RVQELTGRSVEFEEMDILDQAALQHLFKKHNFKAVIHFAGLKAVGESVQK  100

101 PLDYYRVNLTGTIQLLEIMKAHGVKNLVFSSSATVYGNPQYLPLDEAHPT  150
    |||||||||||||||||||:||:.|||||||||||||.  :  :.  .|
101 PLDYYRVNLTGTIQLLEIMRAMGVKSLVFSSSATVYGKP.VPASGRGPPH  149

151 GGCTNPYGKSKFFIEEMIRDLCQADKTWNAVLLRYFNPTGAHASGCIGED  200
    ..|.|||||||||||||||.||.|.|:||||||||| |.|||  :|||
150 RGCTKPYGKSKFFIEEMIQDLCRADTAWNAVLLRYFIPIGAHRSARIGED  199

201 PQGIPNNLMPYVSQVAIGRREALNVFGNDYDTEDGTGVRDYIHVVDLAKG  250
    |||||||||||||||||||||||||||||:||.||||||||||||||||
200 PQGIPNNLMPYVSQVAIGRREALNVFGDDYATEDGTGVRDYIHVVDLAKG  249

251 HIAALRKLKEQCGCRIYNLGTGTGYSVLQMVQAMEKVSGKKIPYKVVARR  300
    ||||||||||||||||||||||||||||||||||||:.|||||||||||
250 HIAALKKLKEQCGCRIYNLGTGTGYSVLQMVQAMEKASGKKIPYKVVARR  299

301 EGDVAVCYANPSLAQEELGWTAALGLDRMCEDLWRWQKQNPSGFGTQA   348
    |||||.:|||||||.||||||||||||||||||||||||||||:|.::
300 EGDVAACYANPSLAHEELGWTAALGLDRMCEDLWRWQKQNPSGLGAHG   347
```

HUMAN URIDINE DISPHOSPHATE GALACTOSE-4-EPIMERASE

This application is a Divisional, claiming benefit of priority under 35 U.S.C. § 120, of Application No. 09/113,536, filed Jul. 10, 1998, now U.S. Pat. No. 6,153,739, issued Nov. 28, 2000; which is a Continuation, claiming benefit of priority under 35 U.S.C. § 120, of Application No. 08/462,966, filed Jun. 5, 1995, now abandoned; which is a continuation claiming claims benefit of priority under 35 U.S.C. § 120 of International Application No. PCT/US95/05785, filed May 11, 1995 and published in the English language; each of which is hereby incorporated by reference in its entirety.

BACKGROUND OF THE INVENTION

Carbohydrates are major sources of energy in animals, plants and many microorganisms. They can also be precursors in the biosynthesis of other compounds, such as fatty acids, triglycerides, and some amino acids. Carbohydrates are also important as structural components of connective tissue, nervous tissue, bacterial cell walls, and nucleic acids.

Disaccharides ingested by higher animals are usually hydrolyzed to their monosaccharide components before absorption into the intestine. For example, sucrose is converted into glucose and fructose, maltose is converted into glucose, and lactose is converted into glucose and galactose in most cases by enzymatic activity. It is these monosaccharides that are eventually used for the biosynthesis of carbohydrates. The L forms of the monosaccharides are of small consequence and it is the D form which are most often utilized in the biosynthesis of carbohydrates.

Galactose is an important precursor in carbohydrate biosynthesis and the synthesis of many other macromolecules which are vital to the normal functioning of a mammalian system.

Uridine diphosphate-galactose (UDP-galactose)is also an important intermediate in the metabolism of free D-galactose, formed by the enzymatic hydrolysis of lactose or milk sugar in the intestinal tract. D-galactose is converted into D-glucose in the liver by two series of reactions which have attracted much attention because they are subject to genetic defects in man, resulting in different forms of the hereditary disease galactosemia. Galactosemia results from three known forms of deficiency, galactokinase deficiency, galactose-1-phosphate uridyltransferase deficiency and UDP-galactose-4-epimerase deficiency.

In the liver, free D-galactose is first phosphorylated at carbon atom 1 by galactokinase, to yield D-galactose-1-phosphate, which is converted into UDP-galactose by one of two possible reactions. The minor route is catalyzed by UTP galactose-1-phosphate uridyltransferase.

The UDP-galactose so formed is normally converted into UDP glucose by UDP-galactose-4-epimerase. These reactions make it possible for the galactose residue to enter into the main pathways of glucose metabolism, since UDP-glucose, as we shall see, can donate its glucose residue to glycogen. This uridyltransferase is present in high amounts in the liver of adults but lacking in infants.

The second pathway for utilization of free galactose also begins with galactose 1-phosphate. It is catalyzed by UDP-glucose: galactose 1-phosphate uridyltransferase. This particular enzyme is present in normal fetal liver but is lacking in infants with one form of galactosemia. Such infants are thus unable to utilize galactose by either pathway. Galactosemic infants have an excessively high concentration of D-galactose in the blood and suffer from cataracts of the lens of the eye, mental disorders, impairment of the peripheral nervous system, blindness, hearing deficiency, organomegaly, deranged liver function, including elevated blood galactose, galactosuria, hyper-cholbremic acidosis, albuminuria and aminoaciduria (Mason, H. H. and Turner, M. E., Am. J. Dis. Child, 50:359 (1935) and Komrower, G. M. et al., Arch. Dis. Child, 31:254 (1956)).

Mental retardation is the most significant outcome of galactosemia. The extent of retardation is characterized in that extremely low IQ values result. Psychological problems also seem to be prevalent, with inadequate drive, shyness and withdrawal (Nadler, H. L., et al., Galactosemia, Springfield, Ill., Charles C. Thomas, p. 127 (1969) and Komrower, G. M. and Lee D. H., Arch. Dis. Child, 45:367 (1970)). Other results include a high incidence of ovarian failure with hypergonadotrophic hypogonadism in females who have had adequate dietary therapy (Kaufman, F. R. et al., N. Engl. J. Med., 305:994 (1981); Steinmann, B. et al., N. Engl. J. Med., 305:464 (1981); Kaufman, F. R., et al., J. Inherited Metab. Dis., 9:140 (1986); Robinson, A. C. R., et al., Br. J. Obstet. Gynaecol., 91:199 (1984); and Fraser, I. S., et al., Clin. Reprod. Fertil., 4:133 (1986)). These deficiencies are only a few of the deficiencies which result from this disease and there are numerous other disorders and anatomical and biological problems which result from this disease. The second type of galactosemia is similar to the first type with minor variations in the biological causes and resulting diseases.

Uridine diphosphate galactose-4-epimerase is the third enzyme in the metabolism of dietary galactose and the key enzyme in de novo synthesis of galactose metabolites from glucose (Gitzelmann, R., and Steinmann, B., *Enzyme*, 32:37–46, (1984)). UDP galactose-4-epimerase catalyzes a reversible transaction between UDP-glucose and UDP-galactose, and a deficiency of this enzyme results in galactosemia.

The first case of epimerase deficiency was documented in 1972 by Gitzelmann in the blood cells of an apparently healthy infant (Gitzelmann, R., *Helv. Paediat. Acta*, 27:125–130 (1972)). Subsequent clinical findings indicated that severe clinical manifestations of galactosemia were usually observed in patients with generalized epimerase deficiency and were indistinguishable from the classic galactosemia caused by galactose-1-phosphate uridyltransferase deficiency (Henderson, M. J., and Holton, J. B., *J. Inher. Metab. Dis.*, 6:17–20 (1983)). The incidence of complete absence of epimerase activity in circulating blood cells in estimated to be 1 in 23,000 in Japan (Misumi, H. et al., *Clinica Chimica Acta*, 116:101–105 (1981)). Somatic cell hybrid studies have defined an area from chromosome 1 pter-p21 that likely contains a gene for galactose epimerase (Benn, P. A. et al., *Cytogenet. Cell Genet.*, 24:138–142 (1979) and Lin, M. S. et al., *Cytogenet. Cell Genet.*, 24:217–223 (1979)).

Galactosemia in general is inherited as an autosomal recessive trait. Also, the enzyme may be present, but non-functional due to a mutation in the gene sequence encoding the functional enzyme.

SUMMARY OF THE INVENTION

The gene of the present invention has been putatively identified as a human UDP-galactose-4-epimerase. This identification has been made as a result of amino acid sequence homology to the rat galE MRNA for UDP-galactose-4-epimerase.

In accordance with one aspect of the present invention, there are provided novel mature polypeptides as well as biologically active and diagnostically or therapeutically useful fragments, analogs and derivatives thereof.

In accordance with another aspect of the present invention, there are provided isolated nucleic acid molecules encoding the polypeptide of the present invention, including mRNAs, DNAS, cDNAs, genomic DNAs as well as analogs and biologically active and diagnostically or therapeutically useful fragments thereof.

In accordance with yet a further aspect of the present invention, there are provided processes for producing such polypeptides by recombinant techniques comprising culturing recombinant prokaryotic and/or eukaryotic host cells, containing a nucleic acid sequence encoding the polypeptide of the present invention under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, to treat galactosemia, cataracts, mental disorders, impairment of the peripheral nervous system, blindness, hearing deficiency and organomegaly.

In accordance with yet a further aspect of the present invention, there are also provided nucleic acid probes comprising nucleic acid molecules of sufficient length to specifically hybridize to the polypeptide of the present invention.

In accordance with yet a further aspect of the present invention, there are provided antibodies against such polypeptides.

This invention also provides a method to diagnose human UDP galactose-4-epimerase deficiency which comprises isolating a nucleic acid sample from an individual and assaying the sequence of said nucleic acid sample with the referenced gene of the invention and comparing differences between said sample and the nucleic acid of the instant invention, wherein said differences indicate mutations in the human UDP galactose-4-epimerase gene isolated from an individual.

This invention also provides a method for treating conditions which are related to insufficient human UDP galactose-4-epimerase activity via gene therapy. An additional reference gene comprising the UDP galactose-4-epimerase gene of the instant invention is inserted into a patient's cells either in vivo or ex vivo. The referenced gene is expressed in transfected cells and as a result, the protein encoded by the referenced gene corrects the defect thus permitting the transfected cells to function normally and alleviate disease conditions (or symptoms).

In accordance with yet a further aspect of the present invention, there are provided processes for utilizing such polypeptides, or polynucleotides encoding such polypeptides, for in vitro purposes related to scientific research, synthesis of DNA, manufacture of DNA vectors and the treatment and diagnosis of human disease.

These and other aspects of the present invention should be apparent to those skilled in the art from the teachings herein.

The following drawings are illustrative of embodiments of the invention and are not meant to limit the scope of the invention as encompassed by the claims.

BRIEF DESCRIPTION OF THE FIGURES

FIGS. 1A–B illustrates the cDNAs and corresponding deduced amino acid sequence of the polypeptide of the present invention. The standard one letter abbreviation for amino acids are used.

FIG. 2 is an illustration of the amino acid sequence homology between the polypeptide of the present invention (top) and the rat UDP-galactose 4-epimerase (bottom).

In accordance with an aspect of the present invention, there is provided an isolated nucleic acid (polynucleotide) which encodes for the mature polypeptide having the deduced amino acid sequence of FIGS. 1A–B (SEQ ID NO:2) or for the mature polypeptide encoded by the cDNA of the clone deposited as American Type Culture Collection (ATTC) Deposit # 97112 on April 12, 1995. The ATCC is located at 10801 University Boulevard, Manassas, Va. 20110-2209, USA.

The polynucleotide of this invention was discovered in a cDNA library derived from a human endometrial tumor. It is structurally related to the epimerase family. It contains an open reading frame encoding a protein of 348 amino acid residues. The protein exhibits the highest degree of homology to the rat epimerase gene with over 85% identity over the entire amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–B (SEQ ID NO:1) or that of the deposited clone or may be a different coding sequence which coding sequence, as a result of the redundancy or degeneracy of the genetic code, encodes the same mature polypeptide as the DNA of FIGS. 1A–B (SEQ ID NO:1) or the deposited cDNA.

The polynucleotide which encodes for the mature polypeptide of FIGS. 1A–B (SEQ ID NO:2) or for the mature polypeptide encoded by the deposited cDNA may include, but is not limited to: only the coding sequence for the mature polypeptide; the coding sequence for the mature polypeptide and additional coding sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–B (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–B (SEQ ID NO:2) or the same mature polypeptide encoded by the cDNA of the deposited clone as well as variants of such polynucleotides which variants encode for a fragment, derivative or analog of the polypeptide of FIGS. 1A–B (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–B (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexa-histidine tag supplied by a pQE60 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions-preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 85%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–B (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described which may or may not retain activity. Such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least an 85% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a human UDP galactose-4-epimerase polypeptide which has the deduced amino acid sequence of FIGS. 1A–B (SEQ ID NO:2) or which has the amino acid sequence Decoded by the deposited cDNA, as well as fragments, analogs and derivatives of such polypeptide.

The terms "fragment," "derivative" and "analog" when referring to the polypeptide of FIGS. 1A–B (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–B (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature pqlypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 85% similarity (preferably a 85% identity) to the polypeptide of SEQ ID NO:2 and more preferably a 90% similarity (more preferably a 90% identity) to the polypeptide of SEQ ID NO:2 and still more preferably a 95% similarity (still more preferably a 95% identity) to the polypeptide of SEQ ID NO:2 and to portions of such polypeptide with such portion of the polypeptide generally contains at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide.

Fragments or portions of the polypeptides of the present invention may be employed for producing the corresponding full-length polypeptide by peptide synthesis, therefore, the fragments may be employed as intermediates for producing the full-length polypeptides. Fragments or portions of the polynucleotides of the present invention may be used to synthesize full-length polynucleotides of the present invention.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 85% similarity (preferably at least 85% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID-NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the human UDP galactose-4-epimerase genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicate and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator.

The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or *Bowes melanoma*; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, PXT1, pSG (Stratagene) pSVK3, pBPV, PMSG, pSVL (Pharmacia). However, any other plasmid or vector may be used as long as they are replicate and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CKV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides of the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The human UDP galactose-4-epimerase gene and gene products of the present invention may be employed to treat galactosemia. In the event of an autosomal inherited defect preventing biosynthesis of human UDP galactose-4-epimerase or synthesis of a non-functional human UDP galactose-4-epimerase, the polypeptide of the present invention may be administered to catalyze the reversible reaction between galactose and glucose. Accordingly, all of the undesired diseases and defects resulting from altered galactose levels and altered glucose levels are alleviated by administration of the human UDP galactose-4-epimerase of the present invention.

For example, the human UDP galactose-4-epimerase may be employed to treat cataracts, mental disorders, impairment of the peripheral nervous system, blindness, hearing deficiency, organomegaly, deranged liver function, galactosuria, hypercholoremic acidosis, albuminuria and aminoaciduria.

The human UDP galactose-4-epimerase gene of the present invention will assist in the differentiation of epimerase deficiency galactosemia from galactosemia caused by galactose-1-phosphate uridyltransferase or galactokinase deficiency. Galactosemia caused by epimerase deficiency requires a different treatment, as compared to other forms of the disorder, in that small amounts of dietary galactose must be supplied for the biosynthesis of galactoproteins and galactolipids which require UDP-galactose as precursor. In the transferase or galactokinase deficiency galactosemia, the much needed UDP-galactose can be converted from UDP-glucose via epimerase action.

The polynucleotides and polypeptides of the present invention may be employed as research reagents and materials for discovery of treatments and diagnostics to human disease.

This invention provides a method of screening compounds to identify those which effect the interaction of human UDP galactose-4-epimerase with its substrate. As an example, a mammalian cell such as monkey kidney cells (COS cells) and/or a fibroblast cell line is transfected with a recombinant expression vector containing the cDNA of the present invention encoding for human UDP galactose-4-epimerase. The cells are then contacted with labeled galactose in the presence of the-compound to be screened. Galactose may be labeled such as by radioactivity. Any glucose which is formed from the labeled galactose may then be measured. For example, glucose may be isolated by methods known in the art such as affinity chromatography and the like and liquid scintillation counting may be used to measure the volume of glucose. This amount of glucose may be measured against the amount of glucose produced in a control assay lacking the compound to be screened.

The polypeptides of the present invention and compounds as described above, may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention or compounds may be employed in conjunction with other therapeutic compounds.

The pharmaceutical compositions may be administered in a convenient manner such as by the oral, topical, for example, in an eye drop solution, intranasal or intradermal routes. Parenteral administration, for example, intravenous, intraperitoneal, intramuscular and subcutaneous are particularly preferred. The polypeptide may also be surrounded by a membrane-bound vesicle, such as a liposome. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The human UDP galactose-4-epimerase genes may also be employed in accordance with the present invention by expression of polypeptides encoded by the human UDP galactose-4-epimerase gene in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

The retroviral plasmid vectors may be derived from retroviruses which include, but are not limited to, Moloney Murine Sarcoma Virus, Moloney Murine Leukemia Virus, spleen necrosis virus, Rous Sarcoma Virus and Harvey Sarcoma Virus.

In a preferred embodiment the retroviral expression vector, pMV-7, is flanked by the long terminal repeats (LTRs) of the Moloney murine sarcoma virus and contains the selectable drug resistance gene neo under the regulation of the herpes simplex virus (HSV) thymidine kinase (tk) promoter. Univque EcoRI and HimdIII sites facilitate the introduction of coding sequence (Kirschmeier, P. T. et al., DNA, 7:219-25 (1988)).

The vectors include one or more suitable promoters which include, but are not limited to, the retroviral LTR; the SV40 promoter; and the human cytomegalovirus (CKV) promoter described in Miller, et al., *Biotechnicrues*, Vol. 7, NO:9, 980–990 (1989), or any other promoter (e.g., cellular promoters such as eukaryotic cellular promoters including, but not limited to, the histone, po1 III, and β-actin promoters). The selection of a suitable promoter will be apparent to thsoe skilled in the art from the teachings contained herein.

The nucleic acid sequence encoding the polypeptide of the present invention is under the control of a suitable promoter which includes, but is not limited to, viral thymidine kinase promoters, such as the Herpes Simplex thymidine kinase promoter; retroviral LTRs, the β-actin promoter, and the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therap*, Vol. 1, pg. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

Examples of packaging cells which may be transfected include, but are not limited to, the PE501, PA317 and GP+am12. The vector may transduce the packaging cells through any means known in the art. Such means include, but are not limited to, electroporation, the use of liposomes, and $CaPO_4$ precipitation.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced, include but are not limited to, fibroblasts and endothelial cells.

This invention is also related to the use of the human UDP galactose-4-epimerase gene as a diagnostic. Detection of a mutated form of human UDP galactose-4-epimerase will allow a diagnosis of a disease or a susceptibility to a disease awhich results from underexpression of human UDP galactose-4-epimerase, for example, galactosemia. Individuals carrying mutations in the human UDP galactose-4-epimerase gene may be detected at the DNA level by a variety of techniques. Nucleic acids for diagnosis may be obtained from a patient's cells including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding human UDP galactose-4-epimerase can be used to identify and analyze human UDP galactose-4-epimerase mutations. For example, deletions and insertions can be detected by a change in size of the amplified product in comparison to the normal genotype. Point mutations can be identified by hybridizing amplified DNA to radiolabeled human UDP galactose-4-epimerase RNA or alternatively, radiolabeled human UDP galactose-4-epimerase antisense DNA sequences. Perfectly matched sequences can be distinguished from mismatched duplexes by RNase A digestion or by differences in melting temperatures (Tm). Such a diagnostic would be particularly useful for prenatal and even neonatal testing.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags. Cloned DNA segments may also be used as probes to detect specific DNA segments. The sensitivity of this method is greatly enhanced when combined with PCR. The presence of nucleotide repeats may correlate to a change in human UDP galactose-4-galactokinase activity (causative change) or serve as a marker for various polymorphisms.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)). In addition, sequence alterations, in particular small deletions, may be detected as changes in the migration pattern of DNA heteroduplexes in non-denaturing gel electrophoresis (i.e., heteroduplex electrophoresis) (see, e.g., Nagamine et al., *Am. J. Hum. Genet.*, 45:337–339 (1989)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization (e.g., heteroduplex electroporation, see, White et al., *Genomics*, 12:301–306 (1992), RNase protection (e.g., Meyers et al., *Science*, 230:1242 (1985), chemical cleavage (e.g., Cotton et al., *PNAS. USA*, 85:4397–4401 (1985), direct DNA sequencing, or the use of restriction enzymes, (e.g., Restriction Fragment Length Polymorphisms (RFLP)) in which variations in the number and size of restriction fragments can indicate insertions, deletions, presence of nucleotide repeats and other mutations which create or destroy an endonuclease restriction sequence). Southern blotting of genomic DNA may also be used to identify large (i.e., greater than 100 base pairs) deletions and insertions.

In addition to more conventional gel electrophoresis, and DNA sequencing, mutations (e.g., microdeletions, aneuploidies translocations, inversions) can also be detected by in situ analysis (see, e.g., Keller et al., *DNA Probes, 2d Ed., Stockton Press, N.Y., New York, USA* (1993)). That is, DNA (or RNA) sequences and cells can be analyzed for mutations without isolation and/or immobilization onto a membrane. Fluorescence in situ hybridization (FISH) is presently the most commonly applied method and numerous reviews of FISH have appeared. See e.g., Trachuck et al., *Science*, 250:559–562 (1990) and Trask et al., *Trends, Genet.*, 7:149–154 (1991) which are incorporated herein by reference for background purposes. Hence, by using nucleic acids based on the structure of specific genes, e.g., UDP galactose-4-epimerase, one can develop diagnostic tests for epimerase deficiency.

In addition, some diseases are a result of, or are characterized by, changes in gene expression which can be detected by changes in the mRNA. Alternatively, the UDP galactose-4-epimerase gene can be used as a reference to identify individuals expressing a decreased level of epimerase, e.g., by Northern Blotting or in situ hybridization.

In addition to more conventional gel-electrophoresis and DNA sequencing, mutations can also be detected by in situ analysis.

The present invention also relates to a diagnostic assay for detecting altered levels of human UDP galactose-4-epimerase protein in various tissues since an under-expression as compared to normal control tissue samples allows the detection of galactosemia, or the susceptibility to contraction of galactosemia. Assays used to detect levels of human UDP galactose-4-epimerase protein in a sample derived from a host are well-known to those of skill in the art and include radioimmunoassays, competitive-binding assays, Western Blot analysis and preferably an ELISA assay. An Elisa assay initially comprises preparing an antibody specific to the human UDP galactose-4-epimerase antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any human UDP galactose-4-epimerase proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to human UDP galactose-4-epimerase. Unattached reporter antibody is then washed out. Peroxidase substrates are then added to the dish and the amount of color developed in a given time period is a measurement of the amount of human UDP galactose-4-epimerase protein present in a given volume of patient sample when compared against a standard curve.

Monoclonal antibodies raised against the human UDP galactose-4-epimerase gene product will be useful in quantifying the amount of epimerase in red blood cells, fibroblast skin cells and other cell types.

A competition assay may be employed wherein antibodies specific to human UDP galactose-4-epimerase are attached to a solid support and labeled human UDP galactose-4-epimerase and a sample derived from the host are passed over the solid support and the amount of label detected attached to the solid support can be correlated to a quantity of human UDP galactose-4-epimerase in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

To determine the precise chromosomal location of the human UDP galactose-4-epimerase gene fluorescence in situ hybridization was performed to human chromosome metaphase spreads (Lawrence, J. B. et al., Cell, 52:51–61 (1988) and Johnson, C. V., et al., *Methods in Cell Biology*, 35:73–99 (1991(b))). Approximately 20 spreads were analyzed by eye, most of which had a doublet signal characteristic of genuine hybridization on at least one chromosome, which was chromosome 1. Doublet-signal was not detected on any other chromosome. Detailed analysis of 26 individual spreads, using a combination of fractional length measurements and fluorescence banding, combined with high-resolution image analysis, indicated that the human UDP galactose-4-epimerase gene is positioned within bands 1p34.3–36.1, which precisely coincides with the disease locus of epimerase deficiency galactosemia.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a agarose gel to isolate the desired fragment.

Size separation of the cleaved fragments is performed using 1 percent agarose gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of Human UDP Galactose-4-epimerase

The DNA sequence encoding human UDP galactose-4-epimerase, ATCC # 97112 was initially amplified using PCR oligonucleotide primers corresponding to the 5' and 3' end sequences of the human UDP galactose-4-epimerase gene. Additional nucleotides corresponding to the human UDP galactose-4-epimerase gene were added to the 5' and 3' end sequences, respectively. The 5' oligonucleotide primer has the sequence 5' TCCAAGGTGCCATGGCAGAG 3' (SEQ ID NO:3) contains an Nco I restriction enzyme site at the starting codon of human UDP galactose-4-epimerase coding sequence. The 3' sequence 5'GCGCAGATCTCCTCA-GACTTGCGTGTCACA 3' (SEQ ID NO:4) contains complementary sequences to a BglII site (in bold) and is followed by 20 nucleotides of human UDP galactose-4-epimerase sequence located 3' to the human UDP galactose-4-epimerase DNA insert. The restriction enzyme sites correspond to the restriction enzyme sites on the bacterial expression vector pQE60, (Qiagen, Inc. Chatsworth, Calif.). pQE60 encodes antibiotic resistance (Amp$^r$), a bacterial origin of replication (ori), an IPTG-regulatable promoter operator (P/O), a ribosome binding site (RBS), a 6-His tag and restriction enzyme sites. pQE60 was then digested with NcoI and BglII. The amplified sequences were ligated into pQE60 and were inserted in frame with the sequence encoding for the histidine tag and the RBS. The ligation mixture was then used to transform E. coli strain M15/rep4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized human UDP galactose-4-epimerase was purified from this solution by chromatography on a Nickel-Chelate column under conditions that allow for tight binding by proteins containing the 6-His tag (Hochuli, E. et al., J. Chromatography 411:177–184 (1984)). Human UDP galactose-4-epimerase (90% pure was eluted from the column in 6 molar guanidine HCl pH 5.0 and for the purpose of renaturation adjusted to 3 molar guanidine HC1, 100 mM sodium phosphate, 10 mmolar glutathione (reduced) and 2 mmolar glutathione (oxidized). After incubation in this solution for 12 hours the protein was dialyzed to 10 tmmolar sodium phosphate.

EXAMPLE 2

Cloning and Expression of Human UDP Galactose-4-epimerase using the Baculovirus Expression System The DNA sequence encoding the full length human UDP galactose-4-epimerase protein, ATCC # 97112, is amplified using PCR oligonucleotide primers corresponding to the 5' and 3' sequences of the gene:

The 5' primer has the sequence 5' AAAAGATCTCCCGC-CATCATG GCAGAGAAGGTGCTG 3' (SEQ ID NO:5) and contains a BglII restriction enzyme site (in bold) followed by 8 nucleotides resembling an efficient signal for the initiation of translation in eukaryotic cells (Kozak, M., J. Mol. Biol., 196:947–950 (1987) which is just behind the first 18 nucleotides of the human UDP galactose-4-epimerase gene (the initiation codon for translation "ATG" is underlined).

The 3' primer has the sequence 5' AAATCTAGATCAG-GCT TGCGTGCCAAAGCC 3' (SEQ ID NO:6) and contains the cleavage site for the restriction endonuclease XbaI (in bold) and 21 nucleotides complementary to the 3' sequence of the human UDP galactose-4-epimerase gene. The amplified sequences are isolated from a 1% agarose gel using a commercially available kit ("Geneclean, " BIO 101 Inc., La Jolla, Calif.). The fragment is then digested with the endonucleases BglII and XbaI and then purified again on a 1% agarose gel. This fragment is designated F2.

The vector pA2 (modification of pVL941 vector, discussed below) is used for the expression of the human UDP galactose-4-epimerase protein using the baculovirus expression system (for review see: Summers, M. D. and Smith, G. E. 1987, A manual of methods for baculovirus vectors and insect cell culture procedures, Texas Agricultural Experimental Station Bulletin NO:1555). This expression vector contains the strong polyhedrin promoter of the *Autographa californica* nuclear polyhedrosis virus (ACMNPV) followed by the recognition sites for the restriction endonucleases. The polyadenylation site of the simian virus (SV)40 is used for efficient polyadenylation. For an easy selection of recombinant virus the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid is digested with the restriction enzymes BamHI and XbaI and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. *E. coli* HB101 cells are then transformed and bacteria identified that contained the plasmid (pBac human UDP galactose-4-epimerase) with the human UDP galactose-4-epimerase gene using PCR. The sequence of the cloned fragment is confirmed by DNA sequencing.

5 µg of the plasmid pBac human UDP galactose-4-epimerase is co-transfected with 1.0 µg of a commercially available linearized baculovirus ("BaculoGold® baculovirus DNA", Pharmingen, San Diego, Calif.) using the lipofection method (Felgner et al. Proc. Natl. Acad. Sci. USA, 84:7413–7417 (1987)).

1µg of BaculoGold® virus DNA and 5 µg of the plasmid pBac human UDP galactose-4-epimerase are mixed in a sterile well of a microtiter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution the virus is added to the cells and blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-human UDP galactose-4-epimerase at a multiplicity of infection (MOI) of 2. Six hours later the medium is removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) are added. The cells are further incubated for 16 hours before they are harvested by centrifugation and the labelled proteins visualized by SDS-PAGE and autoradiography.

EXAMPLE 3

COS Cell Expression of Recombinant Human UDP Galactose-4-epimerase

The expression of the plasmid, human UDPgalactose-4-epimerase HA is derived from a vector pcDNAI/Amp (Invitrogen) containing: 1) SV40 origin of replication, 2) ampicillin resistance gene, 3) *E.coli* replication origin, 4) CKV promoter followed by a polylinker region, an SV40 intron and polyadenylation site. A DNA fragment encoding the entire human UDP galactose-4-epimerase precursor and a HA tag fused in frame to its 3' end is cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding human UDP galactose-4-epimerase, ATCC # 97112 is constructed by PCR using two primers: the 5' primer 5, AAAAGATCTCCCGCCATCATG-GCAGAGAAGGTG CTG 3' (SEQ ID NO:7) contains a BglII site (in bold) followed by 18 nucleotides of human UDP galactose-4-epimerase coding sequence starting from the initiation codon; the 3' sequence 5' AAATCTAGAC-TAAGCGTAGTCTGGGACGTCGTATGGG-TACTCCTGGGGGCTTGC GTGCCAAAGCC 3' (SEQ ID NO:8) contains complementary sequences to an XbaI site (in bold), translation stop codon, HA tag and the last 18 nucleotides of the human UDP galactose-4-epimerase coding sequence (not including the stop codon). Therefore, the PCR product contains a BglII site, human UDP galactose-4-epimerase coding sequence followed by HA tag fused in frame, a translation termination stop codon next to the HA tag, and an XbaI site. The PCR amplified DNA fragment are digested with BglII and XbaI, and the vector, pcDNAI/Amp, is digested with BamHI and XbaI restriction enzymes and ligated. The ligation mixture is transformed into $E.$ $coli$ strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant human UDP galactose-4-epimerase, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the human UDP galactose-4-epimerase HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media is then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with an HA specific monoclonal antibody. Proteins precipitated are analyzed on 15% SDS-PAGE gels.

EXAMPLE 4

Expression Pattern of Human UDP Galactose-4-epimerase in Human Tissue

Northern blot analysis is carried out to examine the levels of expression of human UDP galactose-4-epimerase in human tissues. Total cellular RNA samples are isolated with RNAzoll® B system (Biotecx Laboratories, Inc. Houston, Tex.). About 10 µg of total RNA isolated from each human tissue specified is separated on 1% agarose gel and blotted onto a nylon filter (Sambrook, Fritsch, and Maniatis, Molecular Cloning, Cold Spring Harbor Press, (1989)). The labeling reaction is done according to the Stratagene Prime-It kit with 50 ng DNA fragment. The labeled DNA is purified with a Select-G-50 column (5 Prime - 3 Prime, Inc. Boulder, Colo.). The filter is then hybridized with radioactive labeled full length human UDP galactose-4-epimerase gene at 1,000,000 cpm/ml in 0.5 M $NaPO_4$, pH 7.4 and 7% SDS overnight at 65° C. After wash twice at room temperature and twice at 60° C. with 0.5 ×SSC, 0.1% SDS, the filter is then exposed at −70° C. overnight with an intensifying screen.

EXAMPLE 5

Expression of Human UDP Galactose-4-epimerase via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219-25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

A sub-fragment of the human UDP galactose-4-epimerase cDNA is amplified using PCR primers as follows: 5' AAA-GAATTC CCCGCCATCATGGCAGAGAAGGTGCTG 3' (SEQ ID NO:9) containing an EcoRI site (in bold) followed by 18 base pairs of 5' coding region, and a 3' primer having the sequence 5' AAAAAGCTTTCAG GCTTGCGTGC-CAAAGCC 3' (SEQ ID NO:10) contains a HindIII site (in bold) and is followed by 21 base pairs of of 3' sequence.

Equal quantities of the Moloney murine sarcoma virus linear backbone and the EcoRI and HimdIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the human UDP galactose-4-epimerase gene properly inserted.

The amphotropic pA317 or GP+am12 packaging cells are grown in tissue culture to confluent density in Dulbeccol's Modified Eagles Medium (DMEM) with 10% calf serum (CS), penicillin and streptomycin. The MSV vector containing the human UDP galactose-4-epimerase gene is then added to the media and the packaging cells are transduced with the vector. The packaging cells now produce infectious viral particles containing the human UDP galactose-4-epimerase gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produced the human UDP galactose-4-epimerase protein product and the biological actions of human UDP galactose-4-epimerase are conveyed to the host.

Numerous modifications and variations of the present invention are possible in light of the above teachings and, therefore, within the scope of the appended claims, the invention may be practiced otherwise than as particularly described.

What is claimed is:

1. An isolated protein having uridine diphosphate galactose-4-epimerase activity comprising an amino acid sequence selected from the group consisting of:

(a) amino acid residues 1 to 348 of SEQ ID NO:2; and
   (b) amino acid residues 2 to 348 of SEQ ID NO:2.

2. The isolated protein of claim 1 which comprises amino acid sequence (a).

3. The isolated protein of claim 1 which comprises amino acid sequence (b).

4. The isolated protein of claim 1 wherein the amino acid sequence comprises a heterologous polypeptide.

5. The isolated protein of claim 1 wherein said isolated protein is glycosylated.

6. A composition comprising the isolated protein of claim 1.

7. The composition of claim 6, wherein the composition further comprises a liposome.

8. The protein of claim 1 produced by a method comprising:

(a) culturing a host cell expressing the protein under suitable conditions; and
   (b) recovering the expressed protein from the host cell culture.

9. An isolated protein comprising an amino acid sequence selected from the group consisting of:

(a) the amino acid sequence of the full length human uridine diphosphate galactose-4-epimerase polypeptide encoded by the cDNA in ATCC Deposit No. 97112; and
   (b) the amino acid sequence of the full-length human uridine diphosphate galactose-4-epimerase polypeptide, excluding the N-terminal methionine residue, encoded by the human cDNA clone contained in ATCC Deposit No. 97112.

10. The isolated protein of claim 9 which comprises amino acid sequence (a).

11. The isolated protein of claim 9 which comprises amino acid sequence (b).

12. The isolated protein of claim 9 wherein the amino acid sequence comprises a heterologous polypeptide.

13. The isolated protein of claim 9 wherein said isolated protein is glycosylated.

14. A composition comprising the isolated protein of claim 9.

15. The composition of claim 9, wherein the composition further comprises a liposome.

16. The protein of claim 9 produced by a method comprising:

(a) culturing a host cell expressing the protein under suitable conditions; and
   (b) recovering the expressed protein from the host cell culture.

17. A method for the treatment of a patient having need of human UDP galactose-4-epimerase comprising administering to the patient a therapeutically effective amount of the isolated protein of claim 1.

18. A method for the treatment of a patient having need of human UDP galactose-4-epimerase comprising administering to the patient a therapeutically effective amount of the isolated protein of claim 9.

* * * * *

UNITED STATES PATENT AND TRADEMARK OFFICE
CERTIFICATE OF CORRECTION

PATENT NO. : 6,451,577 B1
DATED : September 17, 2002
INVENTOR(S) : Hongjun Ji and Craig A. Rosen It is certified that error appears in the above-identified patent and that said Letters Patent is hereby corrected as shown below:

Title page, Item [54] and Column 1, line 1,
The Title should read: -- HUMAN URIDINE DIPHOSPHATE GALACTOSE-4-EPIMERASE --

Title page,
Item [56], References Cited, OTHER PUBLICATIONS, Reference No. 4 should read:
-- Lin et al., "Assignment of the Gene for Uridine Diphosphate Galactose-4-Epimerase to Human Chromosome 1 by Human-Mouse . . .", Somatic Cell Genetics, 5(3):363-371 (1979). --
    FOREIGN PATENT DOCUMENTS, insert the following additional references:
-- WO        96/35778 A1        11/1996 --
OTHER PUBLICATIONS, insert:
-- Bauer et al., "The isolation, purification and preliminary crystallographic characterization of UDP-galactose-4-epimerase from *Escherichia coli*", Proteins Structure Function and Genetics, 9(2):135-142 (1991).
Beutler, E., "Galactosemia: Screening and diagnosis," Clinical Biochemistry, 24(4):293-300 (1991).
Endres et al., "Cataract and metabolic disease," J. Inher. Metab. Dis., 13(4):509-516 (1990). --

Column 1,
Lines 4 through 13, should read:
-- This application is a Divisional, claiming benefit of priority under 35 U.S.C. § 120, of Application No. 09/113,536, filed July 10, 1998, now U.S. Patent No. 6,153,739, issued November 28, 2000; which is a Continuation, claiming benefit of priority under 35 U.S.C. § 120, of Application No. 08/462,966, filed June 5, 1995, now abandoned; which-claims benefit of priority under 35 U.S.C. § 120 of International Application No. PCT/US95/05785, filed May 11, 1995 and published in the English language; each of which is hereby incorporated by reference in its entirety. --

UNITED STATES PATENT AND TRADEMARK OFFICE
CERTIFICATE OF CORRECTION

PATENT NO. : 6,451,577 B1
DATED : September 17, 2002
INVENTOR(S) : Hongjun Ji and Craig A. Rosen It is certified that error appears in the above-identified patent and that said Letters Patent is hereby corrected as shown below:

<u>Column 1 cont'd,</u>
Line 15, insert:

-- INTRODUCTION
This invention relates to newly identified polynucleotides, polypeptides encoded by such polynucleotides, the use of such polynucleotides and polypeptides, as well as the production of such polynucleotides and polypeptides. The polypeptide of the present invention has been putatively identified as a human uridine diphosphate galactose-4-epimerase. --

Signed and Sealed this

Second Day of September, 2003

JAMES E. ROGAN
*Director of the United States Patent and Trademark Office*

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 1249 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 93..1137

(xi) SEQUENCE DESCRIPTION: SEQ ID NO: 1:

```
GGCACGAGCC GAGCAGGACT CTCCAGTCCT CAGTCACCTT GGACAAAGAA GTGTGGATCC      60

TCAGATTCCA TCTTTTCCAA CTCCAAGGTG CC ATG GCA GAG AAG GTG CTG GTA      113
                                    Met Ala Glu Lys Val Leu Val
                                     1               5

ACA GGT GGG GCT GGC TAC ATT GGC AGC CAC ACG GTG CTG GAG CTG CTG      161
Thr Gly Gly Ala Gly Tyr Ile Gly Ser His Thr Val Leu Glu Leu Leu
         10                  15                  20

GAG GCT GGC TAC TTG CCT GTG GTC ATC GAT AAC TTC CAT AAT GCC TTC      209
Glu Ala Gly Tyr Leu Pro Val Val Ile Asp Asn Phe His Asn Ala Phe
     25                  30                  35

CGT GGA GGG GGC TCC CTG CCT GAG AGC CTG CGG CGG GTC CAG GAG CTG      257
Arg Gly Gly Gly Ser Leu Pro Glu Ser Leu Arg Arg Val Gln Glu Leu
 40                  45                  50                  55

ACA GGC CGC TCT GTG GAG TTT GAG GAG ATG GAC ATT TTG GAC CAG GGA      305
Thr Gly Arg Ser Val Glu Phe Glu Glu Met Asp Ile Leu Asp Gln Gly
                 60                  65                  70

GCC CTA CAG CGT CTC TTC AAA AAG TAC AGC TTT ATG GCG GTC ATC CAC      353
Ala Leu Gln Arg Leu Phe Lys Lys Tyr Ser Phe Met Ala Val Ile His
             75                  80                  85

TTT GCG GGG CTC AAG GCC GTG GGC GAG TCG GTG CAG AAG CCT CTG GAT      401
Phe Ala Gly Leu Lys Ala Val Gly Glu Ser Val Gln Lys Pro Leu Asp
         90                  95                 100

TAT TAC AGA GTT AAC CTG ACC GGG ACC ATC CAG CTT CTG GAG ATC ATG      449
Tyr Tyr Arg Val Asn Leu Thr Gly Thr Ile Gln Leu Leu Glu Ile Met
     105                 110                 115

AAG GCC CAC GGG GTG AAG AAC CTG GTG TTC AGC AGC TCA GCC ACT GTG      497
Lys Ala His Gly Val Lys Asn Leu Val Phe Ser Ser Ser Ala Thr Val
120                 125                 130                 135

TAC GGG AAC CCC CAG TAC CTG CCC CTT GAT GAG GCC CAC CCC ACG GGT      545
Tyr Gly Asn Pro Gln Tyr Leu Pro Leu Asp Glu Ala His Pro Thr Gly
                 140                 145                 150
```

```
GGT TGT ACC AAC CCT TAC GGC AAG TCC AAG TTC TTC ATC GAG GAA ATG      593
Gly Cys Thr Asn Pro Tyr Gly Lys Ser Lys Phe Phe Ile Glu Glu Met
            155                 160                 165

ATC CGG GAC CTG TGC CAG GCA GAC AAG ACT TGG AAC GCA GTG CTG CTG      641
Ile Arg Asp Leu Cys Gln Ala Asp Lys Thr Trp Asn Ala Val Leu Leu
        170                 175                 180

CGC TAT TTC AAC CCC ACA GGT GCC CAT GCC TCT GGC TGC ATT GGT GAG      689
Arg Tyr Phe Asn Pro Thr Gly Ala His Ala Ser Gly Cys Ile Gly Glu
    185                 190                 195

GAT CCC CAG GGC ATA CCC AAC AAC CTC ATG CCT TAT GTC TCC CAG GTG      737
Asp Pro Gln Gly Ile Pro Asn Asn Leu Met Pro Tyr Val Ser Gln Val
200                 205                 210                 215

GCG ATC GGG CGA CGG GAG GCC CTG AAT GTC TTT GGC AAT GAC TAT GAC      785
Ala Ile Gly Arg Arg Glu Ala Leu Asn Val Phe Gly Asn Asp Tyr Asp
                220                 225                 230

ACA GAG GAT GGC ACA GGT GTC CGG GAT TAC ATC CAT GTC GTG GAT CTG      833
Thr Glu Asp Gly Thr Gly Val Arg Asp Tyr Ile His Val Val Asp Leu
            235                 240                 245

GCC AAG GGC CAC ATT GCA GCC TTA AGG AAG CTG AAA GAA CAG TGT GGC      881
Ala Lys Gly His Ile Ala Ala Leu Arg Lys Leu Lys Glu Gln Cys Gly
        250                 255                 260

TGC CGG ATC TAC AAC CTG GGC ACG GGC ACA GGC TAT TCA GTG CTG CAG      929
Cys Arg Ile Tyr Asn Leu Gly Thr Gly Thr Gly Tyr Ser Val Leu Gln
    265                 270                 275

ATG GTC CAG GCT ATG GAG AAG GTC TCT GGG AAG AAG ATC CCG TAC AAG      977
Met Val Gln Ala Met Glu Lys Val Ser Gly Lys Lys Ile Pro Tyr Lys
280                 285                 290                 295

GTG GTG GCA CGG CGG GAA GGT GAT GTG GCA GTC TGT TAC GCC AAC CCC     1025
Val Val Ala Arg Arg Glu Gly Asp Val Ala Val Cys Tyr Ala Asn Pro
                300                 305                 310

AGT CTG GCC CAA GAG GAG CTG GGG TGG ACA GCA GCC TTA GGG CTG GAC     1073
Ser Leu Ala Gln Glu Glu Leu Gly Trp Thr Ala Ala Leu Gly Leu Asp
            315                 320                 325

AGG ATG TGT GAG GAT CTC TGG CGC TGG CAG AAG CAG AAT CCT TCA GGC     1121
Arg Met Cys Glu Asp Leu Trp Arg Trp Gln Lys Gln Asn Pro Ser Gly
        330                 335                 340

TTT GGC ACG CAA GCC T GAGGACCCTC CCCTACCAAG GACCAGGAAA              1167
Phe Gly Thr Gln Ala
    345

AGGAGGAGGT GTCTGCTCTC CAGCCTCTGG GAGGAACTCA GGGCCCTGGA GCTTGTGG    1227

ACAAGACAAG GTCTCCCCTC TC                                           1249
```

(2) INFORMATION FOR SEQ ID NO: 2:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Glu Lys Val Leu Val Thr Gly Gly Ala Gly Tyr Ile Gly Ser
1               5                   10                  15

His Thr Val Leu Glu Leu Leu Glu Ala Gly Tyr Leu Pro Val Val Ile
                20                  25                  30

Asp Asn Phe His Asn Ala Phe Arg Gly Gly Gly Ser Leu Pro Glu Ser
            35                  40                  45

Leu Arg Arg Val Gln Glu Leu Thr Gly Arg Ser Val Glu Phe Glu Glu
        50                  55                  60
```

```
Met Asp Ile Leu Asp Gln Gly Ala Leu Gln Arg Leu Phe Lys Lys Tyr
 65                  70                  75                  80

Ser Phe Met Ala Val Ile His Phe Ala Gly Leu Lys Ala Val Gly Glu
                 85                  90                  95

Ser Val Gln Lys Pro Leu Asp Tyr Tyr Arg Val Asn Leu Thr Gly Thr
            100                 105                 110

Ile Gln Leu Leu Glu Ile Met Lys Ala His Gly Val Lys Asn Leu Val
        115                 120                 125

Phe Ser Ser Ala Thr Val Tyr Gly Asn Pro Gln Tyr Leu Pro Leu
    130                 135                 140

Asp Glu Ala His Pro Thr Gly Gly Cys Thr Asn Pro Tyr Gly Lys Ser
145                 150                 155                 160

Lys Phe Phe Ile Glu Glu Met Ile Arg Asp Leu Cys Gln Ala Asp Lys
                165                 170                 175

Thr Trp Asn Ala Val Leu Leu Arg Tyr Phe Asn Pro Thr Gly Ala His
                180                 185                 190

Ala Ser Gly Cys Ile Gly Glu Asp Pro Gln Gly Ile Pro Asn Asn Leu
        195                 200                 205

Met Pro Tyr Val Ser Gln Val Ala Ile Gly Arg Arg Glu Ala Leu Asn
210                 215                 220

Val Phe Gly Asn Asp Tyr Asp Thr Glu Asp Gly Thr Gly Val Arg Asp
225                 230                 235                 240

Tyr Ile His Val Val Asp Leu Ala Lys Gly His Ile Ala Ala Leu Arg
                245                 250                 255

Lys Leu Lys Glu Gln Cys Gly Cys Arg Ile Tyr Asn Leu Gly Thr Gly
            260                 265                 270

Thr Gly Tyr Ser Val Leu Gln Met Val Gln Ala Met Glu Lys Val Ser
        275                 280                 285

Gly Lys Lys Ile Pro Tyr Lys Val Val Ala Arg Arg Glu Gly Asp Val
    290                 295                 300

Ala Val Cys Tyr Ala Asn Pro Ser Leu Ala Gln Glu Glu Leu Gly Trp
305                 310                 315                 320

Thr Ala Ala Leu Gly Leu Asp Arg Met Cys Glu Asp Leu Trp Arg Trp
                325                 330                 335

Gln Lys Gln Asn Pro Ser Gly Phe Gly Thr Gln Ala
                340                 345
```

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO: 3:

TCCAAGGTGC CATGGCAGAG                                                          20

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single

```
        (D) TOPOLOGY: linear (ii) MOLECULE TYPE: DNA (genomic)

(v) FRAGMENT TYPE: linear (xi) SEQUENCE DESCRIPTION: SEQ ID NO: 4:

GCGCAGATCT CCTCAGACTT GCGTGTCACA                                    30

(2) INFORMATION FOR SEQ ID NO: 5:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (genomic)

(v) FRAGMENT TYPE: linear (xi) SEQUENCE DESCRIPTION: SEQ ID NO: 5:

AAAAGATCTC CCGCCATCAT GGCAGAGAAG GTGCTG                              36

(2) INFORMATION FOR SEQ ID NO: 6:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(v) FRAGMENT TYPE: linear (xi) SEQUENCE DESCRIPTION: SEQ ID NO: 6:

AAATCTAGAT CAGGCTTGCG TGCCAAAGCC                                     30

(2) INFORMATION FOR SEQ ID NO: 7:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (genomic)

(v) FRAGMENT TYPE: linear (xi) SEQUENCE DESCRIPTION: SEQ ID NO: 7:

AAAAGATCTC CCGCCATCAT GGCAGAGAAG GTGCTG                              36

(2) INFORMATION FOR SEQ ID NO: 8:

(i) SEQUENCE CHARACTERISTICS:
         (A) LENGTH: 65 base pairs
         (B) TYPE: nucleic acid
         (C) STRANDEDNESS: single
         (D) TOPOLOGY: linear (ii) MOLECULE TYPE: DNA (genomic)

(v) FRAGMENT TYPE: linear (xi) SEQUENCE DESCRIPTION: SEQ ID NO: 8:

AAATCTAGAC TAAGCGTAGT CTGGGACGTC GTATGGGTAC TCCTGGGGGC TTGCGTGCCA    60
AAGCC                                                               65
```

```
(2) INFORMATION FOR SEQ ID NO: 9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO: 9:

AAAGAATTCC CCGCCATCAT GGCAGAGAAG GTGCTG                                   36

(2) INFORMATION FOR SEQ ID NO: 10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO: 10:

AAAAAGCTTT CAGGCTTGCG TGCCAAAGCC                                          30
```